US011918331B2

(12) United States Patent
Baker et al.

(10) Patent No.: US 11,918,331 B2
(45) Date of Patent: Mar. 5, 2024

(54) MICRO-MOVEMENT AND GESTURE DETECTION USING RADAR

(71) Applicant: Hill-Rom Services, Inc., Batesville, IN (US)

(72) Inventors: Steven D. Baker, Beaverton, OR (US); Jennifer Bergstrom, Portland, OR (US); Heinz-Hermann Dalbert, Charleston, SC (US); Brandon P. Fisk, Brookville, IN (US); Yongji Fu, Harrison, OH (US); Michael S. Hood, Batesville, IN (US); Charles A. Lachenbruch, Batesville, IN (US); John A. Lane, Weedsport, NY (US); Kenzi L. Mudge, Skaneateles, NY (US); Matthew O'Neal, Indianapolis, IN (US); Frank E. Sauser, Cincinnati, OH (US); Douglas A. Seim, Okeana, OH (US); Gregory J. Shannon, Indianapolis, IN (US)

(73) Assignee: Hill-Rom Services, Inc., Batesville, IN (US)

(*) Notice: Subject to any disclaimer, the term of this patent is extended or adjusted under 35 U.S.C. 154(b) by 402 days.

(21) Appl. No.: 17/102,683

(22) Filed: Nov. 24, 2020

(65) Prior Publication Data
US 2021/0169361 A1 Jun. 10, 2021

Related U.S. Application Data

(60) Provisional application No. 62/946,143, filed on Dec. 10, 2019.

(51) Int. Cl.
*A61B 5/05* (2021.01)
*A61B 5/00* (2006.01)
(Continued)

(52) U.S. Cl.
CPC ............. *A61B 5/05* (2013.01); *A61B 5/01* (2013.01); *A61B 5/02007* (2013.01);
(Continued)

(58) Field of Classification Search
CPC ........... A61B 5/05; A61B 5/01; A61B 5/1101; A61B 5/1107; A61B 5/1123;
(Continued)

(56) References Cited

U.S. PATENT DOCUMENTS 7,916,066 B1 * 3/2011 Osterweil ............ A61B 5/1117
382/115
8,376,954 B2 * 2/2013 Lange .................. A61B 5/7275
600/534
(Continued)

FOREIGN PATENT DOCUMENTS

AU 2007329219 A1 * 8/2009 ............... A61B 5/05
CN 103126684 A * 6/2013
(Continued)

OTHER PUBLICATIONS

Van Hoek, Arno and Razzaghi, Elyas, Micro-Shivering Detection: Detection of human micro-shivering using a 77 GHz radar, May 29, 2019, Halmstad University, 2019 (Year: 2019).*
(Continued)

*Primary Examiner* — Joseph M Dietrich
*Assistant Examiner* — Michael T. Holtzclaw
(74) *Attorney, Agent, or Firm* — Merchant & Gould P.C.

(57) ABSTRACT

A movement detection device includes a signal transmission device configured to transmit a radar signal transmission toward a target area and to receive reflected radar signals, and a signal analysis device configured to analyze the reflected radar signals to detect a movement in the target
(Continued)

area that is indicative of micro-shivering. In response to detecting the micro-shivering, the movement detection device generates an alarm.

4 Claims, 5 Drawing Sheets

(51) Int. Cl.
*A61B 5/01* (2006.01)
*A61B 5/02* (2006.01)
*A61B 5/11* (2006.01)
*G01S 7/41* (2006.01)
*G01S 13/88* (2006.01)
*G08B 25/00* (2006.01)
*G06F 3/01* (2006.01)
*G08B 7/06* (2006.01)

(52) U.S. Cl.
CPC .......... *A61B 5/1101* (2013.01); *A61B 5/1107* (2013.01); *A61B 5/1123* (2013.01); *A61B 5/1126* (2013.01); *A61B 5/4205* (2013.01); *A61B 5/4255* (2013.01); *A61B 5/4356* (2013.01); *A61B 5/486* (2013.01); *A61B 5/7246* (2013.01); *A61B 5/725* (2013.01); *A61B 5/746* (2013.01); *G01S 7/415* (2013.01); *G01S 13/886* (2013.01); *G08B 25/00* (2013.01); *A61B 5/4839* (2013.01); *A61B 2562/06* (2013.01); *G06F 3/017* (2013.01); *G08B 7/06* (2013.01)

(58) Field of Classification Search
CPC ... A61B 5/1126; A61B 5/4205; A61B 5/4255; A61B 5/4356; A61B 5/486; A61B 5/725; A61B 5/746; A61B 5/4839; A61B 2562/06; G01S 7/415; G06F 3/017
See application file for complete search history.

(56) References Cited

U.S. PATENT DOCUMENTS

| | | | | |
|---|---|---|---|---|
| 8,403,865 B2 * | 3/2013 | Halperin | .............. | A61N 1/3956 600/584 |
| 8,439,849 B2 | 5/2013 | Lin et al. | | |
| 8,562,526 B2 | 10/2013 | Heneghan et al. | | |
| 8,740,793 B2 | 6/2014 | Cuddihy et al. | | |
| 9,398,884 B2 * | 7/2016 | Tanishima | ........... | A61B 5/1455 |
| 9,788,762 B2 | 10/2017 | Auerbach | | |
| 9,883,809 B2 * | 2/2018 | Klap | ................... | A61B 5/7282 |
| 10,159,435 B1 | 12/2018 | Brankovic | | |
| 11,653,848 B2 * | 5/2023 | Lane | ...................... | A61B 5/024 600/407 |
| 2007/0100666 A1 * | 5/2007 | Stivoric | ................ | A63F 13/211 374/E1.002 |
| 2010/0274145 A1 * | 10/2010 | Tupin, Jr. | ............. | A61B 5/0022 600/511 |
| 2012/0274502 A1 * | 11/2012 | Hyde | ................... | G01S 13/867 342/175 |
| 2013/0245502 A1 | 9/2013 | Lange et al. | | |
| 2013/0278414 A1 * | 10/2013 | Sprigg | .................. | A61B 5/746 340/539.12 |
| 2013/0300573 A1 * | 11/2013 | Brown | .................... | G01S 13/42 340/870.01 |
| 2014/0235965 A1 * | 8/2014 | Tran | ........................ | A61B 8/06 600/407 |
| 2016/0235344 A1 | 8/2016 | Auerbach | | |
| 2018/0184908 A1 * | 7/2018 | Meyerson | ............ | A61B 5/6833 |
| 2018/0207450 A1 | 7/2018 | Sanchez et al. | | |
| 2018/0214091 A1 | 8/2018 | Baker et al. | | |
| 2018/0251122 A1 | 9/2018 | Golston et al. | | |
| 2019/0015277 A1 | 1/2019 | Sauser et al. | | |
| 2019/0053707 A1 * | 2/2019 | Lane | .................... | A61B 5/1116 |
| 2019/0216393 A1 | 7/2019 | Baheti et al. | | |
| 2019/0249053 A1 | 8/2019 | Santra et al. | | |

FOREIGN PATENT DOCUMENTS

| | | | |
|---|---|---|---|
| CN | 103126684 A | 6/2013 | |
| DE | 102013221544 A1 | 4/2015 | |
| EP | 2755720 A1 | 7/2014 | |
| EP | 2983629 A2 | 2/2016 | |
| EP | 3513717 A1 | 1/2018 | |
| JP | 2017108819 A * | 6/2017 | |
| JP | 2017108819 A | 6/2017 | |
| WO | 0215560 A2 | 2/2002 | |
| WO | WO-2010042738 A2 * | 4/2010 | .......... A61B 5/1101 |
| WO | WO-2018136402 A2 * | 7/2018 | ............ G08B 21/02 |
| WO | 2019092133 A1 | 5/2019 | |
| WO | 2019140155 A1 | 7/2019 | |

OTHER PUBLICATIONS

"Arno Van Hoek, Elyas Razzaghi, Micro-Shivering Detection—Detection of human micro-shivering using a 77 GHz radar, May 29, 2019, Halmstad University, Master's Programme in Electronics Design" (Year: 2019).*

European Search Report, Application No. EP 20 21 2226, dated Apr. 29, 2021.

* cited by examiner

MICRO-MOVEMENT AND GESTURE DETECTION USING RADAR

INTRODUCTION

Small ranges of movement such as micro-movements can sometimes indicate a physiological condition of a patient. For example, micro-shivering, peristaltic intestinal motion, jugular vein distension, and pregnancy contractions produce micro-movements that are often not detectable by caregivers without the aid of medical devices that are in contact with the patient.

Prompt medical treatment is important to reduce negative medical outcomes. However, the inability to quickly detect micro-movements that are indicative of a physiological condition delays the response time for treatment, which can lead to negative medical outcomes.

Additionally, it is important to maintain a sterile environment within a healthcare facility. Infection risks can be minimized by eliminating the need to physically touch devices. Also, it is desirable to enable patients to control the devices in their rooms (e.g., bed, TV, temperature control, etc.) without having to locate and physically touch a control device.

SUMMARY

In general terms, the present disclosure relates to a patient movement detection device and method. In one possible configuration and by non-limiting example, the device and method determine a physiological condition or gesture without physical contact. Various aspects are described in this disclosure, which include, but are not limited to, the following aspects.

One aspect relates to a movement detection device that comprises a signal transmission device configured to direct a radar signal transmission toward a target area and to receive reflected radar signals, and a signal analysis device configured to analyze the reflected radar signals to determine a movement. The movement is indicative of a physiological condition or a gesture that is detected based on the reflected radar signals.

In some examples, the movement is indicative of micro-shivering that is detected based on the reflected radar signals, and in response to detecting the micro-shivering, an alarm is generated to mitigate the detected micro-shivering. In some examples, the movement further includes a peristaltic intestinal movement that is detected based on the reflected radar signals, the peristaltic intestinal movement being used by the signal analysis device to determine a bowel movement, an intestinal blockage, or choking. In some examples, the movement further includes jugular vein distension that is detected based on the reflected radar signals, and in response to determining jugular vein distension, an alarm is generated to indicate a risk for heart failure.

In some examples, the signal analysis device determines a contactless blood pressure measurement by measuring a pulse transit time from the reflected radar signals. The pulse transit time is measured from a heartbeat and a distal pulse. The heartbeat is a chest wall movement detected from the reflected radar signals. The distal pulse is a heartbeat induced movement on a skin surface detected from the reflected radar signals. The skin surface is a patient's face.

In some further examples, the signal analysis device detects cardiac deterioration by mapping a heartbeat shape using data from the reflected radar signals. In some examples, the signal analysis device detects pregnancy contraction intensity, frequency, and duration from the reflected radar signals. In some examples, the signal analysis device detects patterns of movement associated with pain management from the reflected radar signals.

In some examples, the signal analysis device recognizes gestures to control the operation of a controllable device. In some examples, the movement detection device is fixed in an area next to touch controls of the controllable device, and is configurable to recognize various hand shapes and movements that are correlated to the touch controls. In some examples, the gestures recognized by the signal analysis device are used to move or position the controllable device, silence an alarm on the controllable, activate functions of the controllable device, deactivate functions of the controllable device, or initiate a call for assistance. In some examples the movement detection device is installed on a patient support system, and the signal analysis device detects gestures that indicate that a caregiver is preparing to help the patient out of the patient support system, and transmits a signal to silence or disarm an exit alarm of the patient support system. In some examples, the movement detection device is installed on a vital signs monitor, and the signal analysis device detects gestures to control the vital signs monitor including to display one or more items of information, to measure one or more vital signs, or to save one or more measured vital signs to an electronic record. In some examples, the signal analysis device detects gestures to control one or more environmental conditions within a subject arrangement area including temperature and lighting. In some examples, the movement detection device controls one or more controllable devices in an operating room to eliminate the need to touch the one or more controllable devices in the operating room.

Another aspect relates to a movement detection device, comprising: a signal transmission device configured to transmit a radar signal transmission toward a target area and to receive reflected radar signals; and a signal analysis device configured to analyze the reflected radar signals to detect a movement in the target area, wherein the movement is indicative of micro-shivering, and wherein in response to detecting the micro-shivering, the movement detection device generates an alarm to mitigate the detected micro-shivering.

Another aspect relates to a method for mitigating micro-shivering, the method comprising: transmitting a radar signal transmission toward a target area; receiving reflected radar signals from the target area; analyzing the reflected radar signals to detect a movement in the target area, the movement being indicative of micro-shivering; and generating an alarm to mitigate the detected micro-shivering.

Another aspect relates to a system for mitigating micro-shivering, the system comprising: a thermal sensor configured to measure a temperature of a target area; and a movement detection device, including: a signal transmission device configured to transmit a radar signal transmission toward the target area and to receive reflected radar signals; and a signal analysis device configured to analyze the reflected radar signals to detect a movement indicative of micro-shivering; and wherein the system generates an alarm when a change in the temperature of the target area occurs after the micro-shivering is detected.

A variety of additional aspects will be set forth in the description that follows. The aspects can relate to individual features and to combination of features. It is to be understood that both the foregoing general description and the following detailed description are exemplary and explana-

DESCRIPTION OF THE FIGURES

The following drawing figures, which form a part of this application, are illustrative of the described technology and are not meant to limit the scope of the disclosure in any manner.

DETAILED DESCRIPTION

This patent application is directed to using radar to detect movements. These movements can be categorized into (1) micro-movements that are indicative of a physiological condition such as micro-shivering, peristaltic intestinal motion, jugular vein distention, and pregnancy contractions; and (2) gestures for controlling one or more types of devices.

Figure 1:
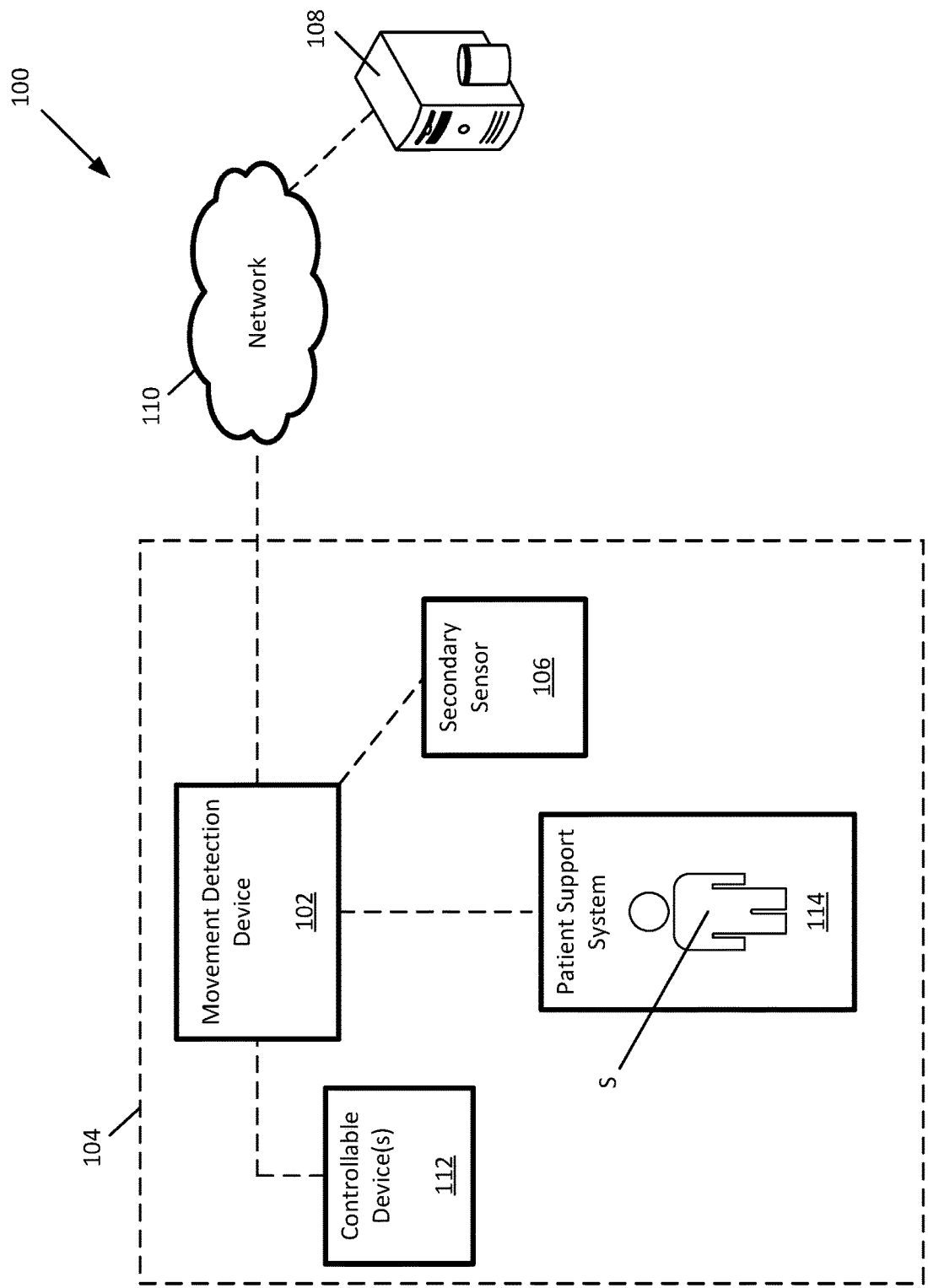
FIG. 1 schematically illustrates an example monitoring system.

FIG. 1 schematically illustrates an example monitoring system 100. The monitoring system 100 includes a movement detection device 102 that detects micro-movements and gestures from a subject S located in a subject arrangement area 104. The movement detection device 102 detects these movements without touching or contacting the subject S.

In some examples, the movement detection device 102 is separately installed within the subject arrangement area 104. In other examples, the movement detection device 102 is incorporated into another device positioned within a close vicinity of the subject S such as a patient support system or a vital signs monitor. Other configurations are possible.

In the example illustrated in FIG. 1, the subject S is a patient in a healthcare facility, and the subject arrangement area 104 is a room within the healthcare facility such as a patient room or an operating room. A patient support system 114 supports the subject S within the subject arrangement area 104. Examples of the patient support system 114 may include a bed on which the patient can lie, rest, or sleep, a surgical table, a stretcher, a chair, a lift, and the like.

In alternative examples, the subject S is a caregiver such as a nurse, physician, doctor, surgeon, and the like. In such examples, the subject arrangement area 104 can be a room within the healthcare facility such as a patient room or an operating room where the subject S performs a task related to providing treatment, taking vitals, or performing a surgery.

In some examples, the movement detection device 102 is a device that is separately installed in the subject arrangement area 104. In some examples, the movement detection device 102 is fixed or otherwise incorporated into another device present in the subject arrangement area 104, such as the patient support system 114 that supports the subject S within the subject arrangement area 104, such as the patient support system described in U.S. Pat. No. 9,259,371 to Zerhusen, which is hereby incorporated by reference. In yet other examples, the movement detection device 102 is fixed or otherwise incorporated into a vital signs monitor that monitors various physiological aspects of the subject S, such as the vital signs monitor described in U.S. Pat. No. 9,265,429 to Pierre, which is hereby incorporated by reference.

In the example monitoring system 100 shown in FIG. 1, the movement detection device 102 communicates with a central station 108 through a data communications network 110. In other example embodiments, it is contemplated that the movement detection device 102 can directly communicate with the central station 108. The central station 108 operates to manage patient data and information for providing continuous patient monitoring, clinical workflows, and alarm management within the healthcare facility.

The data communications network 110 communicates data between one or more computing devices, such as between the movement detection device 102 and the central station 108. Examples of the data communications network 110 include a local area network and a wide area network such as the Internet. In some examples, the data communications network 110 includes wireless communications, wired communications, or a combination of wireless and wired communications. Examples of wireless communications include Wi-Fi communication devices that utilize wireless routers or wireless access points, cellular communication devices that utilize one or more cellular base stations, Bluetooth, ANT, ZigBee, medical body area networks, personal communications service (PCS), wireless medical telemetry service (WMTS), and other similar devices and services.

A secondary sensor 106 is included in the subject arrangement area 104. The secondary sensor 106 is operatively connected to the movement detection device 102 to communicate data to the movement detection device 102, and receive data therefrom. The secondary sensor 106 is used by the monitoring system 100 to provide enhanced feedback on the subject S' condition. In some examples, the secondary sensor 106 is a thermal sensor that detects the subject S's temperature. The temperature readings of subject S obtained from the secondary sensor 106 allow the movement detection device 102 to determine whether detected micro-shivering by the subject S has caused the subject S's core body temperature to increase.

FIG. 1 further illustrates that the movement detection device 102 is operatively connected to communicate with one or more controllable devices 112 within the subject arrangement area 104. As will be described in more detail below, the movement detection device 102 can be used by the monitoring system 100 to detect gestures from the subject S to control the operation of the one or more controllable devices 112 within the subject arrangement area 104.

Figure 2:
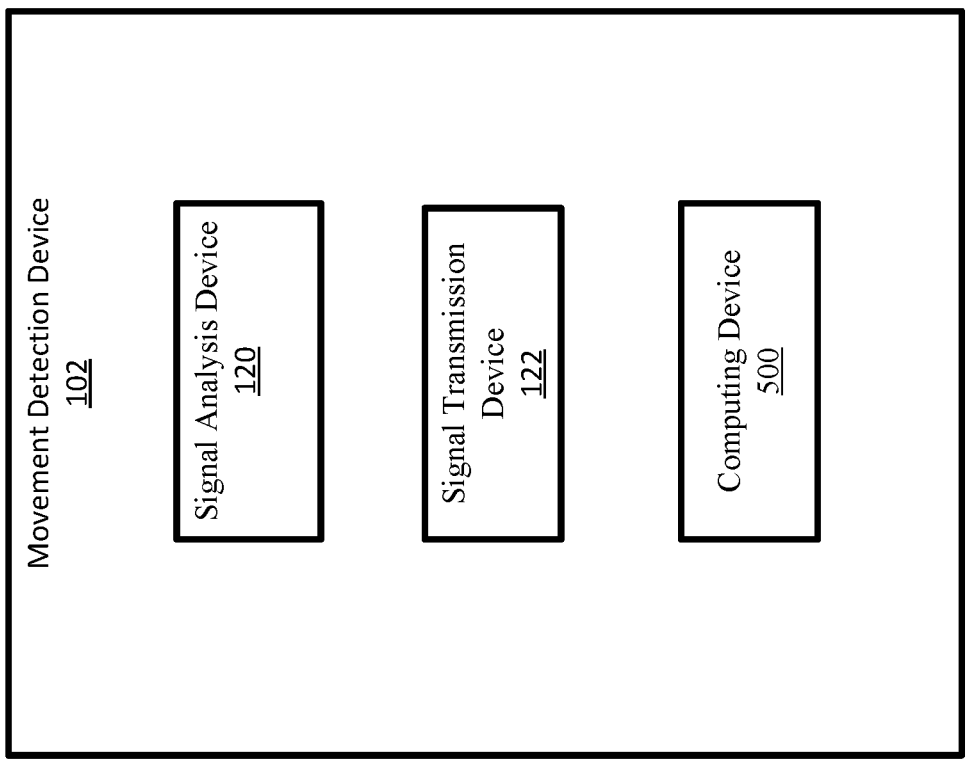
FIG. 2 schematically illustrates an example movement detection device.

FIG. 2 schematically illustrates an example of the movement detection device 102. In the example shown in FIG. 2, the movement detection device 102 includes a signal analysis device 120, a signal transmission device 122, and a computing device 500. In certain examples, the signal transmission device 122 is positioned on an external housing of the movement detection device 102 and the signal analysis device 120 is an internal hardware component of the movement detection device 102 positioned inside the external housing.

In one example, the signal transmission device 122 is a radar signal transceiver that transmits radar signals toward the subject S and receives reflected radar signals. The signal transmission device 122 includes one or more antennas to transmit and receive the radar signals.

The signal analysis device 120 operates to analyze the radar signals received from the signal transmission device 122 to determine a movement of the subject S. In some examples, one or more algorithms are used by the signal analysis device 120 to determine the movement. In some examples, the computing device 500 includes a processor and a memory that control the operation of the signal analysis device 120 and the signal transmission device 122.

Figure 3:
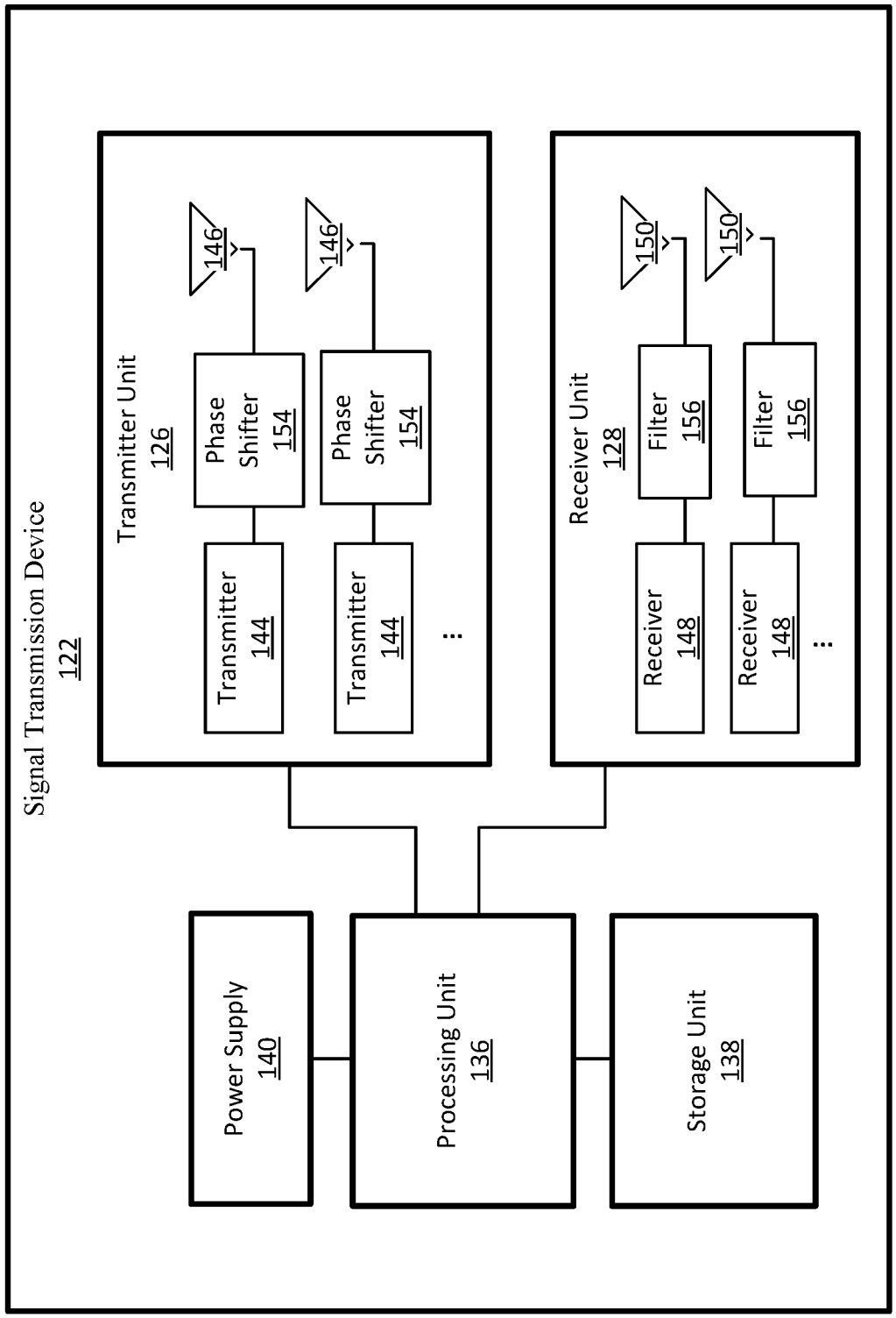
FIG. 3 schematically illustrates an example signal transmission device.

FIG. 3 schematically illustrates an example configuration of the signal transmission device 122. In this example, the signal transmission device 122 is a radar module that uses radar signals to detect various characteristics of the subject S within the subject arrangement area 104. The signal transmission device 122 includes a transmitter unit 126, a receiver unit 128, a processing unit 136, a storage unit 138, and a power supply 140. In certain aspects, the signal transmission device 122 incorporates components of the patient monitoring system described in U.S. patent application Ser. No. 15/679,570 filed on Aug. 17, 2017, and the vital sign detection and measurement system described in U.S. Patent Application No. 62/798,124 filed on Jan. 29, 2019, the entireties of which are hereby incorporated by reference.

In some examples, the signal transmission device 122 is a phased array that electronically steers the transmitter unit 126 and receiver unit 128. In alternative examples, the signal transmission device 122 uses automatic target recognition (ATR) to mechanically steer the transmitter unit 126 and receiver unit 128 by recognizing characteristics of a target such as the subject S located in the subject arrangement area 104. In some examples, reflected radar signals received by the transmitter unit 126 are used to recognize the characteristics of the target for steering the transmitter unit 126. Alternatively, or in combination with the reflected radar signals received by the transmitter unit 126, an external device such as a camera can be used to recognize the characteristics of the target for steering the transmitter unit 126.

The transmitter unit 126 includes one or more signal transmitters 144 to produce radar signals, and one or more transmitting antennas 146 to transmit the radar signals toward a target area such as the subject arrangement area 104 where the subject S is located. The signal transmitters 144 emit radar signals (also referred to as radio waves or electromagnetic waves) in predetermined directions through the transmitting antennas 146. In some examples, signal transmitters 144 use pulsed frequency chirping at predetermined time intervals.

The radar signals produced from the signal transmitters 144 are fed to the transmitting antennas 146 through phase shifters 154, controlled by the processing unit 136, which alter the phase of the radar signals electronically, to steer the radar signals to different directions. The algorithm stored in the storage unit 138 can be used to adjust the focus of the radar signals transmitted from the transmitting antennas 146 by controlling the dispersion of the radar signals in a particular direction. Electronically controlling the direction and focus of the radar signals emitted from the transmitting antennas 146 reduces noise and improves the signal strength. In some examples, the phase shifters 154 may also be incorporated in the receiver unit 128.

The radar signals transmitted from the transmitting antennas 146 reflect off objects, such as the subject S and surrounding objects in the subject arrangement area 104, and return to the receiver unit 128. The receiver unit 128 includes one or more signal receivers 148 and one or more receiving antennas 150 for receiving the reflected radar signals. In some examples, the same antennas can be used for both the receiving antennas 150 and the transmitting antennas 146. The receiver unit 128 can be arranged in the same location as, or adjacent to, the transmitter unit 126. In certain examples, the reflected signals captured by the receiving antennas 150 can be strengthened by electronic amplifiers and/or signal-processed to recover useful radar signals.

A plurality of signal transmitters 144, a plurality of transmitting antennas 146, a plurality of signal receivers 148, and a plurality of receiving antennas 150 can be used to transmit signals to different directions or angles, and receive reflected signals from different directions or angles, thereby detecting different objects and/or different portions of a single object, which can be used to map different objects and/or different portions of an object within a target area that is being monitored by the signal transmission device 122.

The reflected radar signals received by the receiver unit 128 are delayed versions of the radar signals transmitted from the transmitter unit 126. The radar signals that are reflected back towards the receiver unit 128 are used to measure a movement of the subject S such as by monitoring changes in the frequency of the radar signals, caused by the Doppler effect, due to an object moving toward or away from the signal transmission device 122 and to measure the range, caused by the delay in the received signal. In some examples, the scale of the movement is small and the effect is a micro-Doppler effect. The terms Doppler effect and micro-Doppler effect are used interchangeably. In this manner, the phase of the reflected radar signals is monitored to measure micro-movements of the subject S without having to contact the subject S.

Various types of radar signals can be used by the signal transmission device 122. In one example, the signal transmission device 122 uses millimeter waves (also referred to as mmWaves or millimeter band), which are in the spectrum between about 30 GHz and about 300 GHz. Millimeter waves are also known as extremely high frequency (EHF) waves. Millimeter waves have short wavelengths that can range from about 10 millimeters to about 1 millimeter. In some examples, Doppler motion sensing can be performed for detecting micro-movements at lower frequencies (e.g., 2.5 GHz) although gesture, position, and distention detection may have insufficient accuracy from Doppler motion sensing at these lower frequencies.

Still referring to FIG. 3, the processing unit 136 operates to control the transmitter unit 126 and the receiver unit 128. In some examples, the processing unit 136 is further configured to perform the functionalities of the signal analysis device 120, such as processing and analyzing of the radar signals to determine a movement of the subject S.

The storage unit 138 includes one or more memories configured to store data associated with the radar signals and data usable to evaluate the radar signals. The storage unit 138 may also include one or more algorithms to adjust the direction and focus of the radar signal transmission. The storage unit 138 can be of various types, including volatile and nonvolatile, removable and non-removable, and/or persistent media. In some embodiments, the storage unit 138 is an erasable programmable read only memory (EPROM) or flash memory.

The power supply 140 provides power to operate the signal transmission device 122 and associated elements. In some examples, the power supply 140 includes one or more batteries, which is either for single use or rechargeable. In other examples, the power supply 140 includes an external power source, such as mains power or external batteries.

In some examples, filters 156 are used to filter the reflected radar signals to focus on a particular type of movement of the subject S. For example, the filters 156 are used to detect valid movement signals. In some examples, the filters 156 are used to ignore objects that move above or below a predetermined distance or velocity, and to ignore objects that are motionless. Filters 156 may also be used to subtract background objects. The filtering is performed using the reflected radar signals received by the receiver unit 128. In some examples, an external device such as a camera can also be used to detect valid movements of the subject S for enhancing the filtering of the reflected radar signals. Additional methods of detecting valid movement signals such as machine learning and pattern recognition may also be used.

Figure 4:
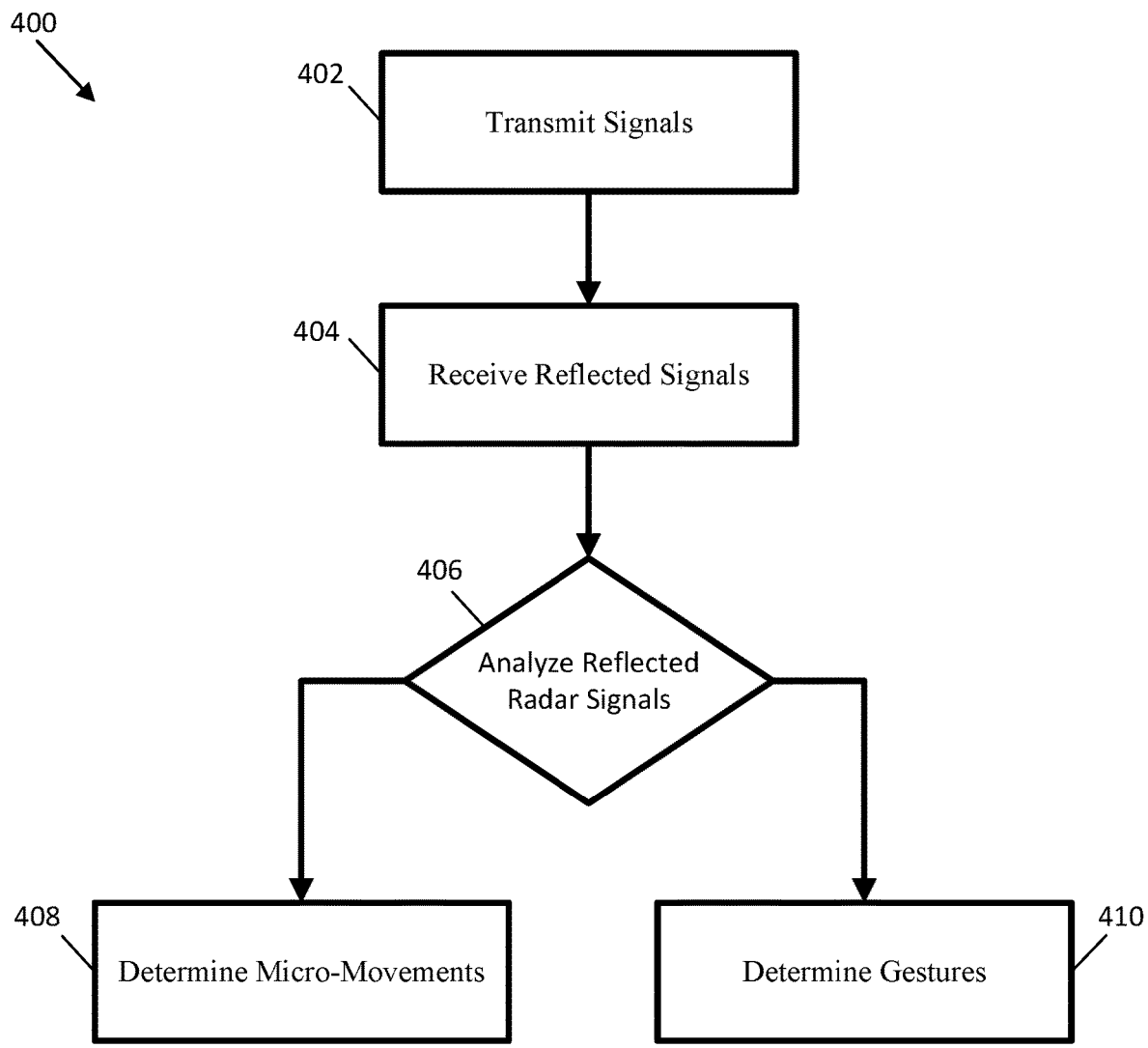
FIG. 4 illustrates a method of determining micro-movements and gestures.

FIG. 4 illustrates a method 400 of detecting a movement of the subject S. In some example embodiments, the method 400 is performed by the movement detection device 102.

As shown in FIG. 4, the method 400 includes an operation 402 of transmitting radar signals. As described above, the movement detection device 102 includes a signal transmission device 122 having a transmitter unit 126 with one or more signal transmitters 144 for producing radar signals and one or more transmitting antennas 146 for transmitting the radar signals toward a target area such as the subject arrangement area 104 where subject S is located.

In some examples, the method 400 uses frequency chirping to transmit the radar signals. In some examples, the method 400 transmits the radar signals using frequency chirping at predetermined time intervals of 50 milliseconds. In some examples, the method 400 transmits millimeter waves in a spectrum between about 30 GHz and about 300 GHz.

Next, the method 400 includes an operation 404 of receiving reflected radar signals. As described above, the signal transmission device 122 of the movement detection device 102 further includes a receiver unit 128 having one or more signal receivers 148 and one or more receiving antennas 150 for receiving the radar signals reflected from the subject S.

Next, the method 400 includes an operation 406 of analyzing data from the reflected radar signals to detect a movement of the subject S. In some examples, the data from the reflected radar signals is transmitted to the central station 108 via the data communications network 110 for further analysis, display, and/or alarm triggering.

In some examples, one or more algorithms are performed by the signal analysis device 120 to detect the movement of the subject S based on the data collected from the reflected radar signals. The data inputted into the one or more algorithms includes frequency changes in the reflected radar signals caused by the Doppler effect. In some examples, operation 406 includes filtering the reflected radar signals by using the filters 156 of the receiver unit 128.

In some examples, the method 400 proceeds to an operation 408 of determining micro-movements indicative of a physiological condition. Micro-shivering, peristaltic intestinal motion, jugular vein distention, and pregnancy contractions are examples of micro-movements that are indicative a physiological condition. By using the data from the reflected radar signals, a physiological condition can be determined and monitored without contacting the subject S.

Alternatively, the method 400 proceeds to an operation 410 of determining gestures indicative of commands for controlling one or more devices within the subject arrangement area 104. Advantageously, by using the data from the reflected radar signals, the commands are detected without the subject S having to contact the one or more devices.

The method 400 may include additional operations to subtract background noise, and thereby improve the quality of the movement detection. For example, the filters 156 described above can be used to remove reflected radar signals outside a predetermined frequency or distance range. The filters 156 can be used to remove reflected radar signals outside of an azimuth or elevation range where the subject S is located. The filters 156 can also be used to subtract out ambient background reflections. In some examples, waveforms of the reflected radar signals can be correlated with an expected shape of a known micro-movement waveform to discriminate against signals that are not representative of a predetermined micro-movement.

A. Shivering and Micro-Shivering

During cardiac surgery, blood flow to the brain is stopped for a period of time. Targeted temperature management (also known as therapeutic hypothermia) is a medical treatment that lowers the core body temperature for a specific duration of time after cardiac surgery has been performed. By lowering the core body temperature, the metabolic rate and oxygen consumption of the brain are lowered in order to maintain normal brain functioning following resuscitation of the patient from cardiac surgery.

Shivering is the body's natural response to lowering the core body temperature. In some instances, shivering is not detectable especially when the patient is covered by clothing, blankets, and the like. Micro-shivering, also known as subclinical shivering, occurs when the muscles start to twitch in an attempt to warm up the body. Micro-shivering is not visibly detectable by caregivers. Instead, caregivers have to know to look for other physiological signs such as unexplained increase in heart rate, the rate of cooling the core body temperature slows down, increased difficulty in keeping the patient cool, evidence of shivering on an electroencephalogram (EEG) monitor, and the like. Shivering and micro-shivering generate heat which causes an increase in core body temperature, metabolic rate, and oxygen consumption, and which can cause irreparable damage to the brain after resuscitation from cardiac surgery.

In certain examples, the movement detection device 102 is installed in a subject arrangement area 104 such as a post-anesthesia care unit (PACU) where patients are admitted following cardiac surgery. In some examples, the movement detection device 102 is a separately installed device. In other examples, the movement detection device 102 is installed into another device such as a vital signs monitor or a patient support system (e.g., a bed, a surgical table, a chair, a lift, a stretcher, etc.) that is located within the PACU.

The movement detection device 102 automatically detects shivering and micro-shivering in patients undergoing targeted temperature management by analyzing the data from the reflected radar signals. Advantageously, the movement detection device 102 detects shivering and micro-shivering through the patient's clothing and bedding, and without contacting the patient. Additionally, the movement detection device 102 is able to provide an objective assessment of whether the patient is shivering or micro-shivering.

The movement detection device 102 can include an aiming device to optimize the aiming and direction of the radar signal transmission from the signal transmission device 122. The aiming device can visually indicate the direction of the radar signal transmission. In some examples, the aiming device is a laser or a light-emitting diode (LED) that emits a visible light in the direction of the radar signal transmission. In this manner, the aiming device can assist a caregiver to direct the signal transmission device 122 towards an appropriate target area (e.g., the subject arrangement area 104), and even more specifically towards a specific anatomical area of the patient. Further, the visible light from the aiming device can provide a visual confirmation to the caregiver that the signal transmission device 122 is pointed in an appropriate direction.

High-pass filtering can be performed to filter out breathing, heart rate, and patient body movement which enhances the sensitivity and accuracy of the shivering and micro-shivering detection. In some examples, a frequency range from about 3 Hz to about 20 Hz is filtered for detecting shivering and micro-shivering from the reflected radar signals. In some examples, only radar signals reflected from a certain portion of the patient's body such as the patient's body core (e.g., torso) are analyzed.

When shivering or micro-shivering is detected by the movement detection device 102, an alarm is generated to alert caregivers to take action to mitigate the shivering and micro-shivering. For example, the alarm can instruct a caregiver to take actions to mitigate and/or stop the shivering and micro-shivering such as administering one or more types of sedatives and neuromuscular blockers to the patient.

In some examples, the alarm is generated by the movement detection device 102. In other examples, the alarm is generated by the central station 108 or by one or more devices associated with the central station 108 after a signal indicating a positive detection of shivering or micro-shivering is sent to the central station 108 via the data communications network 110.

In some examples, the alarm is visibly displayed on a display device of the movement detection device 102 or is visibly displayed on one or more display devices associated with the central station 108. In other examples, the alarm is an audible alarm generated by one or more speakers of the movement detection device 102 or by one or more speakers associated with the central station 108. Additional types of alarms are contemplated.

In some examples, the movement detection device 102 receives a temperature reading from the secondary sensor 106 of the target area where the shivering and/or micro-shivering is detected. The movement detection device 102 can determine whether a change in the temperature reading occurs after the shivering and/or micro-shivering is detected. As described above, an increase in core body temperature can cause irreparable damage to the brain after resuscitation from cardiac surgery Thus, in some examples, the movement detection device 102 can escalate the alarm based on the change in the temperature reading. For example, the alarm can be escalated to have a higher priority over other alarms, and can include a visual or audible indicator that signals to caregivers that the patient's core body temperature has increased due to micro-shivering and instruct the caregivers to mitigate the micro-shivering.

In another illustrative example, the movement detection device 102 can be installed in a subject arrangement area 104 where it is not desirable for the patient to be cold. In this example, the movement detection device 102 generates an alarm to alert caregivers that the patient is cold after the movement detection device 102 detects shivering and/or micro-shivering. The alarm can instruct the caregivers to raise the ambient temperature around the target area where the shivering and/or micro-shivering is detected such as by raising the temperature of the room where the patient is located or bringing additional clothing, blankets, and the like to cover the target area where the shivering and/or micro-shivering is detected to keep the patient warm.

In some further examples, the movement detection device 102 is configurable for use with the secondary sensor 106 (see FIG. 1) to provide enhanced feedback on a patient's condition. For example, the movement detection device 102 can be used along with a thermal imaging device or thermal sensor to determine whether a patient's core temperature is changing when shivering and/or micro-shivering is detected by the movement detection device 102. For example, the secondary sensor 106 can confirm a patient's temperature deterioration when the movement detection device 102 detects micro-shivering during targeted temperature management. When the patient is not undergoing targeted temperature management, the secondary sensor 106 can provide confirmation that the patient is cold when the movement detection device 102 detects that the patient is shivering and/or micro-shivering.

B. Peristaltic Intestinal Movement

In the gastrointestinal tract, smooth muscle tissues contract in sequence to produce a peristaltic wave to propel food along the tract. Peristaltic movement comprises relaxation of circular smooth muscles, then their contraction behind the material to keep it from moving backward, and then longitudinal contraction to push it forward. After food is digested, waste material in the form of feces and urine is eliminated from the gastrointestinal tract.

In one illustrative embodiment, the movement detection device 102 is installed in a subject arrangement area 104 to automatically detect peristaltic intestinal motion using the data from the reflected radar signals. In some examples, the movement detection device 102 is installed in a patient support system (e.g., a bed, chair, surgical table, lift, stretcher, etc.) to automatically and continuously monitor peristaltic movement of the patient.

The movement detection device 102 is configurable to analyze data from the reflected radar signals to monitor bowel movements such as when the patient is ready to defecate, or to monitor bladder fluid level such as when the patient needs to urinate. An alarm can be generated by the movement detection device 102 or central station 108 to notify caregivers that a bowel movement is incoming so that the caregivers can help the patient to the toilet or so that the caregivers can replace a bedpan under the patient support system for bedridden patients.

Additionally, the movement detection device 102 can detect an intestinal blockage or bowel obstruction which prevents the normal peristaltic movement of digestion. In this example, an alarm can be generated by the movement detection device 102 or central station 108 to alert caregivers that the patient is experiencing an intestinal blockage so that the caregivers can provide treatment including providing intravenous fluids, antibiotics, and/or pain medication.

In a further example, the movement detection device 102 is a handheld device that is used in a post-operative recovery ward to detect peristalsis in postoperative patients. When peristalsis is detected, the patient can be released from the healthcare facility (e.g., the patient is classified as outpatient). When peristalsis is not detected, the patient can be admitted to the healthcare facility for further treatment (e.g., the patient is classified as in-patient).

In some examples, the movement detection device 102 detects an obstruction in the peristaltic movement of the upper gastrointestinal tract such as when the patient is choking on food. An alarm can be generated by the movement detection device 102 or central station 108 to alert caregivers that the patient is choking and the need for immediate medical assistance.

In some examples, the movement detection device 102 uses the aiming device (described above) and one or more filtering techniques to enhance the sensitivity and accuracy of the peristaltic movement detection. For example, the aiming device and filtering can be used to ensure that only radar signals reflected from a specific anatomical area of the subject S such as the gastrointestinal tract are analyzed for detecting the peristaltic movement.

C. Jugular Vein Distention

Jugular veins are located on both sides of the neck. Jugular veins act as passageways for blood to move from the head to the superior vena cava which is the largest vein in the upper body. The superior vena cava then transports the blood to the heart and lungs.

Jugular vein distention (JVD) occurs when increased pressure from the superior vena cava causes the jugular vein to bulge. Typically, bulge in the jugular vein is most visible on the right side of the neck. Jugular vein distention (JVD) is thus indicative of a blood volume increase in the superior vena cava, which is a sign of heart failure.

The movement detection device 102 is configurable to use the data from the reflected radar signals to measure the JVD. In some examples, the movement detection device 102 can be implemented into a diagnostic tool for heart failure. For example, the movement detection device 102 can be implemented into a diagnostic tool that can be used at home by patients (i.e., non-physicians) to determine if an emergency room visit is warranted based on the detected JVD.

The movement detection device 102 is configurable to use the data from the reflected radar signals to detect the height of the meniscus in a patient's jugular vein and the location of the clavicle, and measure the distance between the two to determine a JVD measurement. In some further examples, the movement detection device 102 uses these measurements to estimate the central venous pressure of the patient. As an illustrative example, when the movement detection device 102 detects a central venous pressure above 8 cm $H_2O$, the movement detection device 102 generates an alarm to indicate that the patient is at risk for heart failure.

D. Contactless Blood Pressure Measurement

Blood pressure is typically measured by a device that uses an inflatable cuff. The cuff can be uncomfortable for patients, and takes time for caregivers to attach and remove, as well as to inflate and deflate for each time a blood pressure measurement is taken.

The movement detection device 102 is configurable to use the data from the reflected radar signals to detect blood pressure without contacting a patient. Accordingly, the movement detection device 102 can be used as a contactless blood pressure measurement device.

In these examples, the movement detection device 102 uses data from reflected radar signals to determine a pulse transit time which is the time for a pulse wave to travel between two arterial sites. The speed at which this arterial pulse wave travels is directly proportional to blood pressure. Hence, pulse transit time can be used to determine blood pressure. The pulse transit time can be determined by detecting a heartbeat and a subsequent distal pulse of the patient.

The movement detection device 102 is configurable to use the data from the reflected radar signals to detect a heartbeat by measuring the movement of the chest wall. For example, the movement detection device 102 can identify chest movements associated with the apex of the heart pushing against the rib cage when the ventricles of the heart contract.

The movement detection device 102 is also configurable to use data from the reflected radar signals to detect a distal pulse by measuring heartbeat induced movement on a skin surface of the patient. For example, the movement detection device 102 can measure heartbeat induced movement on the face of a patient to detect a distal pulse. In some examples, the movement detection device 102 can measure the heartbeat induced movement on the skin surface using similar techniques such as those described above with respect to detecting shivering and micro-shivering.

In some examples, the detection of the heartbeat and distal pulse by the movement detection device 102 is done by using pulsed, continuous, pulsed Doppler, continuous Doppler, chirped Doppler, continuous-wave Doppler, pulsed-chirped Doppler, and ultra-wide band radar transmission signals from the signal transmission device 122 described above.

In alternative examples, the distal pulse can be detected by using Eulerian Video Magnification (EVM) which uses spatial and temporal processing to emphasize temporal variations in a video sequence. Using EVM, a video sequence is decomposed into different spatial frequency bands, and then a sequence of pixel values over time are applied to a filter to extract a frequency band of interest. The resulting signal is then amplified and added back to the original frames to generate an output video that can be used to measure pulse rate. In this manner, the micro-movement of blood that moves with each heartbeat can be measured on a skin surface of the patient such as the patient's face to detect the distal pulse.

E. Detection of Cardiac Deterioration

The shape of a heartbeat varies with onset of congestive heart failure (CHF). In some examples, the movement detection device 102 is configurable to detect cardiac deterioration by mapping the shape of the heartbeat using the data from the reflected radar signals.

Also, the movement detection device 102 can use the data from the reflected radar signals to detect heart arrhythmia and heart rate variability to further enhance the non-contact measurement of cardiac deterioration.

F. Pregnancy Contraction Intensity

The movement detection device 102 is configurable to use the data from the reflected radar signals to detect pregnancy contraction intensity, frequency, and duration. Advantageously, the movement detection device 102 can monitor pregnancy contractions without contact.

G. Objective Measurement of Pain

When patients experience pain or discomfort they often move or fidget their bodies in an effort to find a more comfortable position to mitigate the pain. For example, when a patient is on the patient support system 114 such as a hospital bed within the subject arrangement area 104, the patient may move, twist, and/or fidget their body and limbs in one or more recognized patterns of movement associated with pain management while on the patient support system.

In one illustrative embodiment, the movement detection device 102 is installed in the subject arrangement area 104 to automatically detect patterns of movement associated with pain management using the data from the reflected radar signals. In some examples, the movement detection device 102 is a device that is separately installed in the subject arrangement area 104, while in other examples, the movement detection device 102 is installed into a patient support system (e.g., a bed, chair, surgical table, lift, stretcher, etc.).

Advantageously, by detecting patterns of movement associated with pain management, the movement detection device 102 can provide an objective measurement of pain. This may help remove subjectivity from the assessment of whether a patient is in pain, and may also help to quantify the level of pain experienced by the patient.

In some examples, the movement detection device 102 uses the aiming device (described above) and one or more filtering techniques to enhance the sensitivity and accuracy for detecting patterns of movement associated with pain management.

H. Identify and Quantify Parkinson's Disease

The movement detection device 102 is configurable to use the data from the reflected radar signals to identify and quantify Parkinson's disease. For example, the movement detection device 102 can be used to identify and quantify symptoms of Parkinson's disease such as tremors, muscle rigidity, and slowness of movement enabling a caregiver to assess the progression of the disease such as on a scale of 1-5 stages. The movement detection device 102 is configurable to measure what zones on a patient's body are sedentary, what zones on the patient's body are shaking, and to what degree. Accordingly, the movement detection device 102 can provide a metric on the symptoms of Parkinson's disease as it progresses.

I. Gesture Recognition

In addition to detecting micro-movements indicative of a physiological condition of a patient, the movement detection device 102 can also use the data from reflected radar signals to detect limb and finger movements to recognize various gestures from caregivers and patients. The gestures can be used by the monitoring system 100 to control the operation of one or more controllable devices 112 within the subject arrangement area 104.

The types of gestures that are recognizable by the movement detection device 102 include movements that are larger than the micro-movements described above. Accordingly, the filtering of the reflected radar signals by the filters 156 can be adjusted to enhance the detection of these larger movements. Also, the aiming device (described above) can be adjusted so that the movement detection device 102 is appropriately aimed for detecting various gestures for controlling the operation of the one or more controllable devices 112.

In some examples, the movement detection device 102 can be fixed to a controllable device 112. For example, the movement detection device 102 can be fixed in an area next to the touch controls of the controllable device 112 to recognize various hand shapes and movements (i.e., "gestures") that are correlated to the touch controls on the device. The gestures recognized by the movement detection device 102 can be used to move the controllable device 112, silence an alarm on the controllable device 112, activate and deactivate certain functions of the controllable device 112, or initiate a call for assistance. Advantageously, by recognizing various gestures for controlling the operation of the controllable device 112, the movement detection device 102 reduces the transfer of bacteria to the touch controls of the device.

In some examples, the controllable device 112 is a patient support system (e.g., a bed, a chair, a surgical table, a lift, a stretcher, etc.), and the movement detection device 102 detects gestures from a caregiver or patient to control the movement and positioning of the patient support system such as raising or lowering the patient support system as directed by one or more types of detected gestures. For example, bed controls are typically provided near the head of the bed. Advantageously, the movement detection device 102 can recognize gestures from more convenient locations. For example, the movement detection device 102 when fixed to a bed can recognize a gesture from a caregiver approaching the bed to indicate that the caregiver is preparing to help the patient out of the bed. After the gesture is recognized, the movement detection device 102 can transmit a signal to silence the bed exit alarm or disarm it.

In another example, the controllable device 112 is a vital signs monitor, and the movement detection device 102 detects gestures to control the operation of the vital signs monitor. For example, the movement detection device 102 can detect gestures to display items of information on the vital signs monitor, measure one or more vital signs, or save the one or more measured vital signs in an electronic record.

In further examples, the movement detection device 102 detects gestures from a patient to control one more environmental conditions within the subject arrangement area 104 such as the temperature or lighting. The movement detection device 102 may also detect gestures to control the operation of one or more controllable devices within the subject arrangement area 104 such as a TV, or to dispatch a caregiver to the subject arrangement area 104 for assistance.

In further examples, the movement detection device 102 can be installed in an operating room to control one or more controllable devices 112 such as a surgical table, or to control the location, intensity, and angle of the lights in the operating room. Advantageously, the movement detection device 102 can help maintain a sterile environment within the operating room by eliminating the need for a surgeon or a surgical nurse to touch the one or more devices in the operating room. In some examples, the movement detection device can detect the breach of a sterile field within the healthcare facility. For example, the movement detection device 102 can use the reflected radar signals to perform body tracking to detect if someone who has not undergone proper sterilization procedures enters the sterile area, or to detect if someone prepared to work within the sterile area has touched something that is not sterile.

Figure 5:
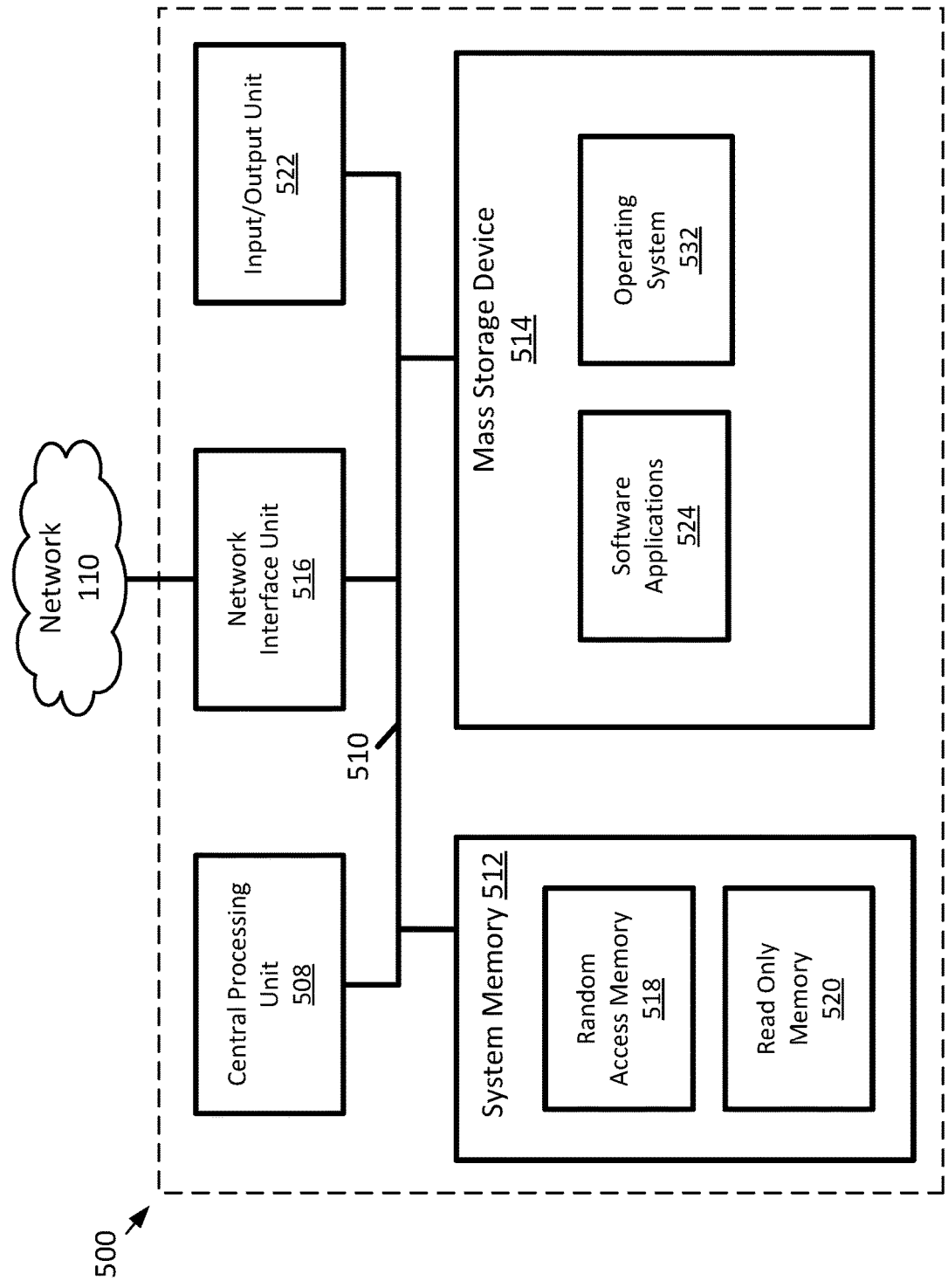
FIG. 5 illustrates an exemplary architecture of a computing device that can be used to implement aspects of the present disclosure.

FIG. 5 illustrates example physical components of a computing device 500, such as the computing device or devices associated with the movement detection device 102 described above. As shown, the computing device 500 includes at least one processor or central processing unit ("CPU") 508, a system memory 512, and a system bus 510 that couples the system memory 512 to the CPU 508. The CPU 508 is an example of a processing device.

The system memory 512 includes a random access memory ("RAM") 518 and a read-only memory ("ROM") 520. A basic input/output system containing the basic routines that help to transfer information between elements within the computing device, such as during startup, is stored in the ROM 520. The computing device further includes a mass storage device 514. The mass storage device 514 is able to store software instructions and data. The mass storage device 514 is connected to the CPU 508 through a mass storage controller connected to the system bus 510. The mass storage device 514 and its associated computer-readable data storage media provide non-volatile, non-transitory storage for the computing device. Although the description of computer-readable data storage media contained herein refers to a mass storage device, such as a hard disk or CD-ROM drive, it should be appreciated by those skilled in the art that computer-readable data storage media can be any available non-transitory, physical device or article of manufacture from which the device can read data and/or instructions. The mass storage device 514 is an example of a computer-readable storage device.

Computer-readable data storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid-state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device.

The computing device 500 may operate in a networked environment using logical connections to remote network devices through the data communications network 110, such as a local network, the Internet, or another type of network. The computing device 500 connects to the data communications network 110 through a network interface unit 516 connected to the system bus 510. The network interface unit 516 may also connect to other types of networks and remote computing systems.

The computing device 500 includes an input/output controller 522 for receiving and processing input from a number of other devices, including a touch user interface display screen, or another type of input device. Similarly, the input/output controller 522 may provide output to a touch user interface display screen, a printer, or other type of output device.

As mentioned above, the mass storage device 514 and the RAM 518 of the computing device 500 can store software instructions and data. The software instructions include an operating system 532 suitable for controlling the operation of the computing device 500. The mass storage device 514 and/or the RAM 518 also store software instructions, that when executed by the CPU 508, cause the computing device 500 to provide the functionality discussed in this document, including the methods described herein.

Communication media may be embodied in the software instructions, data structures, program modules, or other data in a modulated data signal, such as a carrier wave or other transport mechanism, and includes any information delivery media. The term "modulated data signal" may describe a signal that has one or more characteristics set or changed in such a manner as to encode information in the signal. By way of example, communication media may include wired media such as a wired network or direct-wired connection, and wireless media such as acoustic, radio frequency (RF), infrared, and other wireless media.

The block diagrams depicted herein are just examples. There may be many variations to these diagrams described therein without departing from the spirit of the disclosure. For instance, components may be added, deleted or modified.

The description and illustration of one or more embodiments provided in this application are not intended to limit or restrict the scope of the invention as claimed in any way. The embodiments, examples, and details provided in this application are considered sufficient to convey possession and enable others to make and use the best mode of claimed invention. The claimed invention should not be construed as being limited to any embodiment, example, or detail provided in this application. Regardless whether shown and described in combination or separately, the various features (both structural and methodological) are intended to be selectively included or omitted to produce an embodiment with a particular set of features.

Having been provided with the description and illustration of the present application, one skilled in the art may envision variations, modifications, and alternate embodiments falling within the spirit of the broader aspects of the claimed invention and the general inventive concept embodied in this application that do not depart from the broader scope.

What is claimed is:

1. A method for mitigating micro-shivering, the method comprising:
    transmitting a radar signal transmission toward a target area;
    receiving reflected radar signals from the target area;
    analyzing the reflected radar signals to detect a movement in the target area, the movement being indicative of micro-shivering;
    generating an alarm to mitigate the detected micro-shivering;
    receiving a temperature reading from a thermal sensor;
    determining whether a change in the temperature reading occurs after the micro-shivering is detected; and
    escalating the alarm based on the change in the temperature reading determined after the detection of the micro-shivering.

2. The method of claim 1, wherein the alarm instructs a caregiver to mitigate the detected micro-shivering by administering one or more types of sedatives and neuromuscular blockers.

3. The method of claim 1, wherein the alarm instructs a caregiver to mitigate the detected micro-shivering by raising an ambient temperature around the target area.

4. The method of claim 1, wherein analyzing the reflected radar signals includes filtering a frequency range from 3 Hz to 20 Hz to detect the micro-shivering from the reflected radar signals.

* * * * *